United States Patent [19]

Daniels et al.

[11] Patent Number: 5,212,062

[45] Date of Patent: May 18, 1993

[54] **METHOD AND COMPOSITION TO DIRECT *CHLAMYDIA PSITTACI* OR *CHLAMYDIA TRACHOMATIS* INFECTION**

[75] Inventors: Eddie K. Daniels, Hastings, Nebr.; Robert M. Phillips; Teresa J. Yeary, both of Manhattan, Kans.

[73] Assignee: Kansas State University, Manhattan, Kans.

[21] Appl. No.: 755,823

[22] Filed: Sep. 6, 1991

[51] Int. Cl.$^5$ ................ G01N 33/569; G01N 33/571; C07K 15/28

[52] U.S. Cl. .................... 435/7.36; 435/7.32; 435/7.92; 435/7.94; 530/388.4; 530/391.1

[58] Field of Search ............... 435/7.32, 7.36; 530/388.2, 389.5, 825

[56] References Cited

U.S. PATENT DOCUMENTS

| | | |
|---|---|---|
| 4,118,469 | 10/1978 | Caldwell et al. |
| 4,267,170 | 5/1981 | Seawell. |
| 4,271,146 | 6/1981 | Seawell. |
| 4,386,065 | 5/1983 | Waldhalm. |
| 4,427,782 | 1/1984 | Caldwell et al. |
| 4,497,899 | 2/1985 | Armstrong et al. |
| 4,663,291 | 5/1987 | Rose. |
| 4,766,065 | 8/1988 | Mosier et al. |
| 4,916,057 | 4/1990 | Thompson et al. |

FOREIGN PATENT DOCUMENTS

| | | |
|---|---|---|
| 0017460 | 10/1980 | European Pat. Off. |
| 0293079 | 11/1988 | European Pat. Off. |
| 0348725 | 1/1990 | European Pat. Off. |
| 0363106 | 4/1990 | European Pat. Off. |
| 8800977 | 2/1988 | PCT Int'l Appl. |

OTHER PUBLICATIONS

Anderson et al., Efficacy Against Ovine Enzootic Abortin of an Experimental Vaccine Containing Purified Elementary Bodies of *Chlamydia psittaci*, Veterinary Microbiology 24:21-27 (1990).

Chemicon Monoclonal Antibodies & Immunological Reagents Catalog, p. 34 (1989).

Baehr et al, Mapping Antigenic Domains Expressed by *Chlamydia trachomatis* Major Outer Membrane Protein Genes, Proc. Natl. Acad. Sci USA 85:4000-4004 (1988).

Baghian et al, Antibody Response to Epitopes of Chlamydial Major Outer Membrane Proteins on Infectious Elementary Bodies and of the Reduced Polyacrylamide Gel Electrophoresis-Separated Form, Infection and Immunity 58:1379-1383 (1990).

Barron, Microbiology of Chlamydia, CRC Press, Inc. (1988).

Batteiger et al., Antigenic Analysis of the Major Outer Membrane Protein of *Chlamydia trachomatis* with Murine Monoclonal Antibodies, Infectino and Immunity 53:530-533 (1986).

Bavoil et al., Role of Disulfide Bonding in Outer Membrane Structure and Permeability in *Chlamydia trachomatis*, Infection and Immunity 44:479-485 (1984).

Blobel et al., Chlamydia, Handbuch der Bakteriellen Infektionen bei Tieren, Band V. 447-531 (1985).

Brade et al., Chemical, Biological, and Immunochemical Properties of the *Chlamydia psittaci* Lipoplysaccharide, Infection and Immunity 54:568-574 (1986).

Caldwell et al., Antigen Analysis of the Major Outer Membrane Protein of Chlamydia spp., Infection and Immunity 35:1024-1031 (1982).

Caldwell et al., Structural Analysis of Chlamydial Major Outer Membrane Proteins, Infection and Immunity 38:960-968 (1982).

(List continued on next page.)

Primary Examiner—Esther L. Kepplinger
Assistant Examiner—Carol E. Bidwell
Attorney, Agent, or Firm—Tilton, Fallon, Lungmus & Chestnut

[57] ABSTRACT

The present invention relates to a method to detect a Chlamydia infection. More particularly, this invention relates to the discovery of a genus specific antigen in *Chlamydia psittaci* strain DD-34 than can be used to make antibodies that diagnostically identify strains of both *Chlamydia psittaci* and *Chlamydia trachomatis*, while not cross-reacting with other species.

2 Claims, No Drawings

OTHER PUBLICATIONS

Carlson et al., Cloning and Characterization of a *Chlamydia trachomatis* L3 DNA Fragment That Codes for an Antigenic Region of the Major Outer Membrane Protein and Specifically Hybridizes to the C- and C-Related-Complex Serovars, Infection and Immunity 57:487–494 (1989).

Chandler et al. A New Enzyme Immunoassay System Suitable for Field Use and Its Application in a Snake Venom Detection Kit, Clinica Chimica Acta 121:225–230 (1982).

Chandler et al. An Investigation of the Use of Urease-Antibody Conjugates in Enzyme Immunoassays, J. of Immunological Methods 53:187–194 (1982).

Conlon et al. Epitope Mapping with Solid-Phase Peptides: Identification of Type-, Subspecies-, Species- and Genus-Reactive Antibody Binding Domains on the Major Outer Membrane Protein of *Chlamydia trachomatis*, Molecular Microbiology 2(5):673–679 (1988).

Conlan et al. The major outer membrane protein of *Chlamydia trachomatis*: critical binding site and conformation determine the specificity of antibody binding to viable chlamydiae, Molecular Microbiology 3(3):311–318 (1989).

Dopfer et al., Vertraglichkeits- und immunisierungsversuche mit einer kommerziellen Vakzine gegen *Chlamydia psittaci* und *Coxiella burnetii*, Dtsch, tierarztl. Wschr. 93:267–269 (1986).

Favero, Biological Hazards in the Laboratory, Laboratory Medicine 18:665–670 (1987).

Filstein et al., Epidemic of Psittacosis in a College of Veterinary Medicine, JAVMA 179:569–572 (1981).

Fraiz et al., Chlamydial Infectios, Am. Rev. Med. 39:357–370 (1988).

Fudge, Update on Chlamydiosis, Veterinary Clinics of North America: Small Animal Practice 14:201–221 (1984).

Johnson et al. Abortion due to infection with *Chlamydia psittaci* in a sheep farmer's wife, British Medical Journal 290:592–595 (1985).

Johnson et al. Intracerebral Infection of Mice with Ovine Strains of *Chlamydia psittaci*: an Animal Screening Test for the Assay of Vaccines, J. Comp. Path. 96:497–505 (1986).

Kuo et al., Ultrascrutural Study of *Chlamydia trachomatis* Surface Antigens by Immunogold Staining with Monoclonal Antibodies, Infection and Immunity 55:1324–1328 (1987).

Lagrange et al., Vaccines against Mycobacteria and Other Intracellullar Multiplying Bacteria, Ann. Inst. Pasteur/Immunol. 136:151–162 (1985).

Larghi et al. Ethylenimine-Inactivated Rabies Vaccine of Tissue Culture Origin, J. Clin. Microbiology 3:26–33 (1967).

Larghi et al. Rabies Virus Inactivation by Binary Ethylenimine: New Method for Inactivated Vaccine Production, J. Clin. Microbiology 11:120–122 (1980).

Ma et al., Identification of conserved regions for species and subspecies specific epitopes on the major outer membrane protein of *Chlamydia trachomatis*, Microbial Pathogenesis 3:299–307 (1987).

MacDonald, Antigens of *Chlamydia trachomatis*, Reviews of Infectious Diseases 7:731–736 (1985).

Mahajan et al., Development of a Macromolecular Vaccine against Experimental Chlamydiosis and Berberine-a new anti-trachoma agent., 103–109 (1985).

Mohan, Epidemiologic and laboratory observations of *Chlamydia psittaci* infection in pet birds, JAVMA 184:1372–1374 (1984).

Moulder, The relation of the Psittacosis Group (Chlamydiae) to Bacteria and Viruses, Annual Review of Microbiology 20:107–130 (1966).

Nagington, Psittacosis/ornithosis in Cambridgeshire 1975–1983, J. Hyg., Camb. 92:9–19 (1984).

Nano et al., Partial Amino Acid Sequence and Molecular Cloning of the Encoding Gene for the Major Outer Membrane Protein of *Chlamydia trachomatis*, Infection and Immunity 48:372–377 (1985).

Puy et al., Immunological specificity of monoclonal antibodies to *Chlamydia psittaci* ovine abortion strain, Immunology Letters 23:217–222 (1989/1990).

Rank et al., Protective Role of Serum Antibody in Immunity to Chlamydial Genital Infection, Infection Immunity 57:299–301 (1989).

Schachter, Overview of *Chlamydia trachomatis* Infection and the Requirements for a Vaccine, Reviews of Infectious Diseases 7:713–716 (1985).

Seki et al., Monoclonal Antibodies to *Chlamydia psittaci*: Characteristics and Antigenic Analysis, Jpn. J. Vet Sci. 50:383–393 (1988).

Smith et al., A modified ELISA that selectively detects monoclonal antibodies recognizing native antigen, J. of Immunological Methods 94:31-35 (1986).

Stephens et al. A species-specific major outer membrane protein domain, 110-113.

Stephens et al. High-Resolution Mapping of Serovar-Specific and Common Antigenic Determinants of the Major Outer Membrane Protein of *Chlamydia trachomatis*, J. Exp. Med. 167:817-831 (1988).

Storz, Chlamydia and Chlamydia-Induced Diseases (Charles C. Thomas Publishers 1971).

Su et al., Differential Effect of Trypsin on Infectivity of *Chlamydia trachomatis*: Loss of Infectivity Requires Cleavage of Major Outer Membrane Protein Variable Domains II and IV, Infection and Immunity 56:2094-2100 (1988).

Tan et al., Protection of Sheep against *Chlamydia psittaci* Infection with a Subcellular Vaccine Containing the Major Outer Membrane Protein, Infection and Immunity 58:3101-3108 (1990).

Taylor et al., Attempted Oral Immunization with Chlamydial Lipopolysaccharide Subunit Vaccine, Investigative Ophthalmology & Visual Science 28:1722-1726 (1987).

Taylor et al., Oral Immunization with Chlamydial Major Outer Membrane Protein (MOMP), Investigative Ophthalmology & Visual Science 29:1847-1853 (1988).

Toyofuku et al., Monoclonal Antibodies against *Chlamydia psittaci*, Microbiol. Immunol. 30:945-955 (1986).

Wenman et al., *Chlamydia trachomatis* Elementary Bodies Possess Proteins which Bind to Eucaryotic Cell Membranes, J. Bacteriology 165:602-607 (1986).

Yung et al., Psittacosis—a review of 135 cases, The Medical Journal of Australia 148:228-3233 (1988).

Zhang et al, Protective Monoclonal Antibodies Recognize epitopes Located on the Major Outer Membrane Protein of *Chlamydia trachomatis*, J. Immunology 138:575-581 (1987).

Zhang et al., The Low-Molecular-Mass, Cysteine-Rich Outer Membrane Protein of *Chlamydia trachomatis* Possesses Both Biovar- and Species-Specific Epitopes, Infection and Immunity 55:2570-2573 (1987).

Zhong et al, Immunaccessible Peptide Sequences of the Major Outer Membrane Protein from *Chlamydia trachomatis* Serovar C, Infection and Immunity 58:3438-3441 (1990).

Zhong et al, Mapping Antigenic Sites on the Outer Membrane Protein of *Chlamydia trachomatis* with Synthetic Peptides, Infection and Immunity 58:1450-1455 (1990).

METHOD AND COMPOSITION TO DIRECT *CHLAMYDIA PSITTACI* OR *CHLAMYDIA TRACHOMATIS* INFECTION

BACKGROUND OF THE INVENTION

1. Field of the Invention

The present invention relates to a method to detect a Chlamydia infection. More particularly, this invention relates to the discovery of a genus specific antigen of *Chlamydia psittaci* strain DD-34 that can be used to make antibodies which diagnostically identify strains of both *Chlamydia psittaci* and *Chlamydia trachomatis,* while not cross-reacting with other species.

2. Description of the Prior Art

Chlamydia are unique organisms that infect a susceptible host by an infectious particle called an elementary body. An elementary body is small, approximately (350 nm) and is resistant to environmental factors. The organism attaches itself to the host cell and is ingested by a phagocytic process. Schachter, J., Overview of Chlamydia trachomatis Infection and Requirements for a Vaccine, Rev. Inf. Dis. 7:713 (1985).

Chlamydia are of medical and biological interest because of their unique interaction with eukaryotic host cells, and the diverse diseases they cause in man and animals. Blobel, H., T. Schlieber, Handbuch der bacteriellen Infection bei Tieren. Gustav Fisher Verlag Stuttgart, p. 447 (1985). Animals susceptible to *Chlamydia psittaci* infections are widely distributed in the animal kingdom, ranging from wild and domesticated birds and mammals to man. These infections have been identified as a cause of pneumonia, enteritis, encephalitis, conjunctivitis, and polyarthritis; abortions and genital disorders; and clinically unapparent infections. Blobel, H., T. Schlieber, Handbuch der bacteriellen Infection bei Tieren. Gustav Fisher Verlag Stuttgart, p. 447 (1985). Although *Chlamydia psittaci* is considered to be primarily a pathogen of animals other than man several strains have shown varying degrees of zoonotic potential. Filstein, M. R., Ley, A. B., Vernon, M. S., Goffney, A., Glickmen, L. T. Epidemic of Psittacosis in a College of Veterinary Medicine. Jour. of Vet. Med. p. 569–872 (Sep. 15, 1981). Fraiz, J. R., Jones, B., Chlamydial Infections. Ann. Rev. Med. 39:357–70 (1988). Fudge, A. M. Update on Chlamydiosis. Vet. Clin. of N. Amer. Small Animal Practice. 14(2):201–21 (March 1984). Johnson, F. W. A., Matheson, B. A., Williams, H., Laing, A. G., Jandial, V., Davidson-Lamb, R., Halliday, G. J., Hobson, D., Wong, S. Y., Hadley, K. M., Moffat, M. A. J., Poslethwaite, R. Abortion Due to Infection with *Chlamydia psittaci* in Sheep Farmer's Wife. British Med. Jour. 290:592–94 (Feb. 23, 1985). Moran, R. Epidemiologic and Laboratory Observation of *Chlamydia psittaci* Infections in Pet Birds. Jour. of Amer. Vet. Med. Assn. 184(11):1372–4 (Jun. 1, 1984). Nagington, J. Psittacosis/Ornithosis in Cambridgeshire. 1975–1983. Jour. Hyg. Camb. 92:9–19. Yung, A. P., Grayson, M. L., Psittacosis—a Review of 135 Cases. The Med. Jour. of Australia 148:228–33 (Mar. 7, 1988). Favero, M. S., Biological Hazards in the Laboratory. Lab. Med., 18(10):665–70 (October 1987). Filstein, M. R., Ley, A. B., Vernon, M. S., Goffney, A., Glickman, L. T. Epidemic of Psittacosis in a College of Veterinary Medicine. J. Vet. Med. p. 569–72 (Sep. 15, 1981). Fraiz, J. R., Jones, B. Chlamydial Infections. Ann. Rev. Med. 39:357–70 (1988). A Chlamidia strain that affects man is termed *Chlamydia trachmomatis.*

Chlamydial infections are recognized in at least 130 species of birds and the transmission from birds to man is well documented. Various strains of *Chlamydia psittaci* are well recognized as causing disease syndromes in a wide variety of mammalian species and *Chlamydia psittaci* infections in humans have been epidemiologically linked to many of these sources. Fudge, A. M., Update on Chlamydiosis. Vet. Clin. of N. Amer. Small Animal Practice, 14(2):201–21 (March 1984). Moran, R., Epidemiologic and Laboratory Observation of *Chlamydia psittaci* Infections in Pet Birds. Jour. of Amer. Vet. Med. Assn. 184(11):1372–4 (Jun. 1, 1984). Nagington, J. Psittacosis/Ornithosis in Cambridgeshire. 1975–1983. Jour. Hyg. Camb. 92:9–19.

Infections with Chlamydia may produce a minimal antibody response, so low that it may be undetected; also tetracycline markedly reduces the antibody response. Storz, J., Chlamydia and Chlamydia-Induced Diseases. Charles C. Thomas, Springfield, Ill. p. 5–287 (1971). Because of these two factors the numbers of cases of *Chlamydia psittaci* may be greatly underestimated. Nagington, J. Psittacosis/Ornithosis in Cambridgeshire. 1975–1983. Jour. Hyg. Camb. 92:9–19. It is therefore important to have a relatively rapid and dependable antigen test for this pathogen. Most commercially available Chlamydial antigen tests for both *Chlamydia trachomatis* and *Chlamydia psittaci* probe for the genus specific lipopolysaccharide which occupies a relatively small portion of outer membrane.

The present invention relates to the discovery of another genus specific polypeptide that can be used to diagnostically identify strains of *Chlamydia trachomatis* and *Chlamydia psittaci.*

SUMMARY OF THE INVENTION

It is an object of the present invention to detect several strains of *Chlamydia trachomatis* and *Chlamydia psittaci* using an antibody to a 96 kilodalton polypeptide identified in a parrot strain of *Chlamydia psittaci* strain ATCC No. DD-34. It is also an object of this invention to provide a monoclonal antibody to the 96 kilodalton polypeptide of parrot strain DD-34. Still another object of this invention is to provide a monoclonal antibody having the characteristics of an antibody secreted by hybridoma ATCC No. HB10861. This antibody can be used to diagnostically identify *Chlamydia trachomatis* and *Chlamydia psittaci* infections.

DETAILED DESCRIPTION OF THE INVENTION

Reference will now be made in detail to the presently preferred embodiments of the inventions, and the following examples, which serve to explain the principles of the invention.

As noted above, the present invention relates to a method or composition of matter to detect *Chlamydia trachomatis* and *Chlamydia psittaci.* In particular, a 96 kilodalton polypeptide of the parrot strains ATCC No. DD-34 has been discovered by the present inventor as being useful in in vitro diagnostics. It is believed that this polypeptide may serve as an antigenic determinant capable of binding to at least one antibody present in sera of Chlamydia infected animal or human. This antigen would be, therefore, capable of serving as the basis for in vitro diagnostic assay. It should be noted that other related polypeptides, i.e. polypeptides ranging from 40 kilodaltons to 140 kilodaltons of ATCC strain DD-34, may in conjunction with the 96 kilodalton polypeptide, serve as the antigenic determinant capable of binding Chlamydia antibodies in infected sera. These polypeptides may also be used to produce antibodies that immunologically recognize Chlamydia polypeptides in infected sera.

The 96 kilodalton polypeptide was identified by the production, cloning, and screening of over 1600 hybridomas. These hybridomas were produced from the fusion of murine spleen cells that had previously been hyperimmunized with strain DD-34 elementary bodies and AG8 myeloma cells. In particular, one Hybridoma 2-15 E3, ATCC No. HB10861 produces monoclonal antibodies that diagnostically identify strains of both *Chlamydia psittaci* and *Chlamydia trachomatis* isolates when tested by an enzyme linked immunosorbant assay or a nitrocellulose membrane dot blot assay. This antibody will identify the presence of intact or solubilized chlamydial proteins in these assays.

EXAMPLE 1

Hybridoma Production

Whole elementary bodies were inactivated with a 1% solution of binary ethyleneamine at 37° C. for 24 hours (Larghi and Nebel, 1988; Larghi et al., 1976). Residual binary ethyleneamine was inactivated by a 1% solution of sodium thiosulfate (Larghi and Nebel, 1988; Larghi et al., 1976). One ml of inactivated elementary bodies containing 8.9 mg protein was mixed with 1 ml of physiological saline, added to a vial of RIBI adjuvant (ImmunoChem, Hamilton, Mont.) and warmed to 37° C. in a water bath prior to mouse inoculation.

Three-month old female Balb/C mice were injected intraperitoneally with 0.2 ml of the elementary body-adjuvant solution. One injection was given weekly for a total of three injections. A fourth intraperitoneally injection without RIBI adjuvant was given four days before fusion. The hyperimmunized spleen cell were fused with AG8 myeloma cells with the aid of polyethylene glycol. After four fusions and the production of approximately 1,600 hybridomas, 19 were identified as rapid growers. These 19 hybridomas were cloned when appropriate by limiting dilution.

Isotyping and Subisotyping Supernatants

Supernatants from the 19 hybridomas were isotyped using an isotyping kit (Hy Clone Laboratories, Logan, Utah) and subisotyped using a reagent kit (Calbiochem Corp., LaJolla, Calif.), according to the manufacturers' recommended protocols. Briefly, the supernatants were isotyped by coating 96-well plates with 100 μL of a plate coating solution containing 1% goat anti-mouse immunoglobulins. Excess solution was removed by tapping an absorbent paper before filling the wells with a phosphate-buffered saline-surfactant solution to reduce nonspecific binding. Next, 50 μL of phosphate-buffered saline-surfactant and 50 μL of hybridoma supernatant was placed in the wells along with positive and negative controls. A peroxidase conjugate and a substrate composed of a concentrate of citrate buffer containing a 1% urea peroxide was used with 0-phenylene diamine as a chromophobe.

For subisotyping, a plate coating solution containing 1% goat anti-mouse immunoglobulins was used to coat a 96-well plate. The supernatants were diluted with phosphate-buffered saline-surfactant solution and added to the plate. After washing, typing antisera was placed in the wells for testing the supernatants and phosphate-buffered saline-surfactant was used for negative controls. A peroxidase conjugate was used followed by a 1% urea peroxide substrate and 0-phenylene diamine as a chromophobe (Table I). The results of isotyping and subtyping are reported in Table I, below.

TABLE I

Immonoglobulin types and assay reactions of the 19 monoclonal antibodies

| Clone supernatants | Isotype/ subisotype | ELISA | Dot Blot Assays: Native Elementary Bodies proteins | Dot Blot Assays: Solubilize Elementary Bodies proteins |
|---|---|---|---|---|
| 2-1 F10 | IgM | − | − | − |
| 2-15 E3 | IgG1 | + | + | + |
| 2-11 F10 | IgG1 | + | − | − |
| 3-8 C8 | IgM | weak + | − | − |
| 2-11 E9 | IgG2a | weak + | − | − |
| 4-5 F3 | IgG1, IgM | + | − | − |
| 4-6 B6 | IgM | + | − | − |
| 4-7 D10 | IgM | + | − | − |
| 4-8 G11 | IgG3, IgM | weak + | − | − |
| 4-10 B8 | IgM | weak + | − | − |
| 4-11 D8 | IgG3 | + | − | − |
| 4-12 B4 | IgM | + | + | − |
| 4-12 B5 | IgG3, IgM | weak + | − | − |
| 4-14 B9 | IgG3, IgM | + | + | − |
| 4-14 D11 | IgG1 | weak + | − | − |
| 4-16 G3 | IgM | weak + | − | − |
| 4-17 B2 | IgG2b, IgM | + | − | − |
| 4-17 B8 | IgG1, IgM | − | − | − |
| 4-7 D10 | IgM | weak + | − | − |

Enzyme Linked Immunosorbent Assay To Native Proteins

The hybridoma supernatants were further characterized by use of a mouse IgG, enzyme immunoassay, hybridoma screening kit according to the manufacturer's recommendations (Vector Laboratories, Burlingame, Calif.). Briefly, whole elementary bodies of *C. psittaci* strain DD-34 were diluted 1 to 250 in deionized distilled water and 100 μL was placed in each well of a 96-well microtiter plate (Midland Scientific, Inc., Omaha, Nebr.).

The plate was sealed with cellophane tape and placed on a shaker in a 37° C. incubator overnight. Supernatants from each of the 19 hybridomas were diluted 1 to 250 and 100 μL of each was assayed in replicates of 5. The assay was done using a biotintylated anti-mouse IgG in phosphate-buffered saline containing 1% normal bovine serum, followed by an avidin-enzyme system with a 2,2'azino-di (3-ethyl benthiazolin-sulfate) substrate. The results were read on a Bio-Tek EL-380 ELISA Reader at 405 nm (BIO-TEK, Winooski, Vt.) and are reported in Table I.

Expansion and Purification of Elementary Bodies

Elementary bodies (ATCC No. VR854 strain-34) were diluted 1 to 10 in a solution containing 0.218 molar sucrose, 0.0038 M $KH_2PO_4$, 0.0072 M $K_2HPO_4$, and 0.0049 M K phosphate glutamate sucrose. The phosphate glutamate sucrose solution had been autoclaved at 10 pound pressure for ten minutes and the pH adjusted to 7.0 with 2N KOH prior to use. Yolk sacs of 7-day-old specific pathogen-free chicken eggs (Spafus, Inc., Roanoke, Ill.) were injected with 0.4 ml of the 1 to 10 elementary bodies-phosphate glutamate sucrose solution. Embryos that die within three days were discarded and assumed dead of bacterial contamination or trauma.

Yolk sac membranes of all eggs that lived past three days were harvested on day seven, mixed with phosphate glutamate sucrose to make a 20% yolk sac membrane solution, homogenized and centrifuged at 300×G for 10 minutes at 4° C. The centrifugate contained three layers. The middle layer containing the elementary bodies was removed with a pipette and purified through RENOGRAFIN 60 (Squibb, New Brunswick, N.J.) density gradients, consisting of 22 ml of 20% RENOGRAFIN on top of 5 ml of 50% RENOGRAFIN. These gradients were centrifuged at 63,500×G for one hour at 4° C. The elementary body fraction collected at the 50% RENOGRAFIN interface. The elementary bodies were removed by drip fractionation and pelleted through calcium-magnesium-free phosphate-buffered saline by centrifuging at 49,200×G for 20 minutes at 4° C. Each pellet was resuspended in 1 ml of calcium-magnesium-free phosphate-buffered saline and frozen at −70° C.

Dot Blot Assay with Native Chlamydial Proteins

A BIO-RAD Bio-Dot apparatus was used with a 0.2 μL pore size nitrocellulose membrane. The membrane was presoaked in Tris buffered saline consisting of 0.016 M Tris HCl and 0.5 M NaCl, pH 7.5 prior to its placement in the Bio-Dot (Biorad) apparatus. One hundred μL of a 1 to 250 dilution of whole elementary bodies of DD-34 chlamydial proteins inactivated with binary ethylenemine was placed in each well and allowed to gravity flow through the membrane. Next, 200 μL of 1% bovine serum albumen in Tris buffered saline was allowed to gravity flow through the membrane to block any unbound sites. This was followed by two washes with 200 μL of a solution consisting of Tris buffered saline with 0.05% Tween 20. The supernatants from the 19 hybridomas were diluted 1 to 250 in an antibody solution consisting of 1% bovine serum albumin in Tris buffered saline with 0.05% Tween 20. One hundred μL of each diluted supernatant was applied to the membrane in replicates of five and allowed to gravity flow. This was followed by three washes with Tris buffered saline with 0.05% Tween 20. The membrane was removed from the apparatus and washed two more times in a glass dish with Tris buffered saline with 0.05% Tween 20. Next, the membrane was treated with 5 μg of biotintylated secondary antibody in Tris buffered saline with 0.05% Tween 20 and agitated on a shaker platform for 30 minutes. This was followed by two washes with Tris buffered saline with 0.05% Tween 20 and two washes with Tris buffered saline before being incubated in an avidin biotin complex for 30 minutes with gentle shaking. The membrane was washed two times with Tris buffered saline with 0.05% Tween 20 and two times with Tris buffered saline. A diaminobenzidine plus nickel chloride substrate was added. After development, the reaction was stopped by washing with deionized distilled water.

To insure enough protein to be recognized by the antibodies was sticking to the membrane, dilutions of 1 to 10 to 1 to 1,500 were run through a membrane and stained with Jansons Aurodye Forte protein stain (BIOTEK, Winooski, Vt.). The results are reported in Table I.

Dot Blot Assay To Solubilized Proteins

The same protocol for the dot blot to native proteins was followed except the chlamydia elementary bodies were boiled for ten minutes prior to running the assay. The results are reported in Table I. It is apparent from Table I that the only clone to recognize the Chlamydia elementary body proteins in all assays was 2-15 E3. This clone has been assigned ATCC No. HB10861. Out of four fusions and the production of approximately 1,600 hybridomas, 19 hybridoma supernatants reacted with varying degrees in the ELISA to whole chlamydials elementary bodies. After further screening, three supernatants bound to whole elementary bodies by both ELISA and dot blot to nitrocellulose, however, when the elementary bodies were solubilized by boiling for 10 minutes and dot blotted, only the supernatant from hybridoma 2-15 E3 reacted. Apparently, the epitope recognized by this monoclonal antibody was persistent after solubilization while the epitopes recognized by the other three monoclonal antibodies were destroyed or altered in such a way that they were no longer recognized.

SDS-PAGE and Immunoblotting of Strains, DD-34, Borg and Host Proteins

Electrophoresis was done as described by Laemmli (1970). Protein contents of 20 μg of strain DD-34, strain Borg, yolk sac membrane, chick and embryo tissue, and albumin was separated by sodium dodecyl sulfate polyacrylamide gel electrophoresis, transferred to 0.2 μL nitrocellulose (American Bionetics, Inc., Hayward, Calif.) and Western blotted with the monoclonal antibody 2-15 E3 and a polyclonal antibody to evaluate possible cross reactivity of the antibodies.

Electrophoresis sample buffer consisted of 0.121 M Tris base, 0.001 M ethylenediaminetetraacetate, 1% sodium dodecyl sulface. Both 1 mM dithiothreitol and 5% 2 - mercaptoethanol were used alternately during the assays to compare possible differences in blotting obtained using either reducing agent. Prior to loading the gels were pre-run for 30 minutes at 10 ma constant current for each gel and electrophoresis was carried out at 30 ma constant current for each gel until proteins were near the bottom edge. The molecular weight marker lanes were removed and stained with a colloidal gold reagent (Jansens Auro Dye Forte protein stain Olen, Belgium). The test proteins were probed with an immunoperoxidase system and a diaminobenzidine nickel chloride substrate (Vector Laboratories, Burlingame, Calif.).

Both chlamydial strains studied apparently share an antigenic epitope that is recognized by monoclonal 2-15 E3 using an ELISA, and in the native or solubilized form when dot blotted to nitrocellulose, however, this epitope is persistent only in Borg after electrophoresis and transfer. By linerization of the proteins in preparation for sodium dodecyl sulfate polyacrylamide gel electrophoresis, the antigenic polypeptide is apparently altered beyond recognition in strain DD-34 but persists in strain borg; however, there appears to be enough reassociation of the solubilized proteins when dot blotted for the epitope to be recognized in strain DD-34 as well as Borg. The 96 kilodalton protein of strain DD-34 thus appears to be a strong antigen. The epitope recognized by monoclonal antibody 2-15 E3 has been shown to exist in both the binary ethyleniamine inactivated form and the noninactivated form.

Hybridoma 2-15 E3 produces monoclonal antibodies that identify strains of both *Chlamydia psittaci* and *Chlamydia trachomatis* isolates when tested by an enzyme linked immunosorbent assay and a nitrocellulose membrane dot blot assay. By sodium dodecyl sulfate poly acrylamide gel electrophoresis, the target polypeptide of 2-15 E3 was found to be in approximately the 96 kilodalton molecular weight range. The hydridoma that secretes this monoclonal antibody was deposited with the ATCC and assigned No. HB10861.

EXAMPLE 2

ELISA for Chlamydial Antigen

The ELISA for Chlamydial antigen is performed on tissue, conjunctival swabs, fecal swabs, or fecal samples. If the test cannot be run immediately upon receipt of the specimen, the material should be frozen until the test can be set up.

Preparation of Sensitizing Buffer

A Tris buffer is made with 0.06 M Tris buffer: 0.3 M KCL: 0.002 M EDTA, at pH 8.0.

Preparation of Urea-Bromocresol Purple Substrate

Eight mg bromocresol purple is dissolved in 1.48 ml of 0.01 M NaOH. This is diluted to 100 ml with deionized distilled water in a 100 ml volumetric flask. 100 mg of urea and 0.2 mM EDTA are added. The pH is adjusted to 4.8 and the substrate is stored at 4° C. until used.

Preparation of ELISA Plates

IMMULON II ELISA plates are coated with 100 μL per well of a 1-1000 dilution of monoclonal antibody 2-15 E3 in sensitizing buffer. The plates are then sealed with cellophane tape and incubated at 37° C. for two hours. The plates can be stored in the refrigerator for at least one month.

Preparation of Test Samples

A two mm cube of tissue or equivalent amount of feces or excretion to ground and placed in a 1 dram screw cap glass vial containing 2 ml of phosphate-buffered saline and 20 μL of 10% formalin. The tip from culture swabs can be broken off in a vial. The sample vials are then vortexed for 15 seconds. Filter the supernatant through a 0.45 7 μL syringe tip filter prior to testing. It should be noted that wooden swabs are not recommended for Chlamydia assays.

Controls

Positive controls are prepared from RENOGRAFIN (Squibb) gradient purified elementary bodies of *Chlamydia psittaci*.

Phosphate buffered saline is used for a negative control.

Testing Procedure

The monoclonal antibody coated ELISA plates are rinsed three times with phosphate-buffered saline or deionized distilled water. Excess wash can be removed by gently tapping the wells with an absorbent toweling. To block any remaining protein binding sites, 100 μL of 3% (v/v) bovine serum albumin or horse serum in phosphate buffered saline is added to each well. The mixture is incubated for 20 minutes at 37° C. in a humidified chamber. The plates are washed three times with phosphate buffered saline or deionized distilled water and excess wash is removed by inverting and gently tapping on absorbent paper toweling. 100 μL of positive control, negative control and test samples is added in triplicate to the wells. The wells are covered with sealing tape and incubated for two hours at 37° C. in a humidified chamber. The plates are again washed three times to remove excess wash from the wells. 100 μL of a 1-1000 dilution of rabbit anti-DD-34 polyclonal antibody is added to each well. The mixture is incubated for two hours at 37° C. in a humidified chamber. This is followed by three additional washes. Next 100 μL of a 1-175 dilution of anti-rabbit urease conjugated antibody (Sigma) is added to each well. The plate is covered and incubated for two hours at 37° C. in a humidified chamber. This is followed by three washes with deionized distilled water. It should be noted that deionized distilled water for washes at this stage because the color development indicated by the presence of bromocresol purple is a function of a change in pH. The use of buffer washes at this stage can result in false positives. Next 100 μL of urea-bromocresol purple (Sigma), pH 4.2 is added to each well. The reaction is allowed to proceed at room temperature for one hour. If an amber color develops, the test is negative and a purple color indicates a positive test. The color development can be stopped with 0.1% thimerosal.

The monoclonal antibody secreted by clone ATCC No. HB10861 was found to be able to detect a variety of *Chlamydia psittaci* strains: B577, 1PA, Borg, E58 (McNutt), CP-3, Texas Turkey, No. 1, and *Chlamydia trachomatis* strains: TWAR 434, LGV-Type II all obtained from the american type culture collection and KSU89-3720, KSU88-15974 and KSU89-13400 isolated by Kansas State University. The present invention relates to a method to detect a Chlamydia infection. More particularly, this invention relates to the discovery of a genus specific antigen in *Chlamydia psittaci* strain DD-34 than can be used to make antibodies that diagnostically identify strains of both *Chlamydia psittaci* and *Chlamydia trachomatis,* while not cross reacting with other species.

It appears from these studies that the 96 kilodalton peptide is an epitope present on various strains of Chlamydia in different animals that is capable of immunologic stimulation.

As this invention may be embodied in several forms without departing from the spirit or essential characteristics thereof, the present embodiment is therefore illustrative and not restrictive, and since the scope of the invention is defined by the appended claims, all changes that fall within the metes and bounds of the claims or that form their functional as well as conjointly cooperative equivalents are therefore intended to be embraced by those claims.

I claim:

1. A monoclonal antibody produced by a hybridoma having all the identifying characteristics of hybridoma ATCC No. HB10861.

2. A method to detect *Chlamydia psittaci* or *Chlamydia trachomatis* antigen in a sample comprising:

(a) contacting a sample with a monoclonal antibody produced by a hybridoma all the identifying characteristics of hybridoma ATCC No. HB10861 affixed to a solid support for a time and under conditions sufficient to form an immune complex on said support;

(b) contacting said support with an antibody which binds to said antigen in said immune complex for a time and under conditions sufficient for binding to occur;

(c) detecting the presence of said immune complex as an indication of the presence of *Chlamydia psittaci* or *Chlamydia trachomatis* antigen in said sample.

* * * * *

UNITED STATES PATENT AND TRADEMARK OFFICE
CERTIFICATE OF CORRECTION

PATENT NO. : 5,212,062

DATED : May 18, 1993

INVENTOR(S) : Daniels et al.

It is certified that error appears in the above-identified patent and that said Letters Patent is hereby corrected as shown below:

On title page, item [54] and col. 1, line 1, delete "Direct" and insert -- Detect --.
Column 2, line 65, before "Chlamydia" insert -- a --; line 67 after "for" insert -- an --.
Column 3, line 54, delete "an" and insert -- on --.
Column 4, in Table I, delete "Solubilize" and insert -- Solubilized --; line 62, delete "pound" and insert -- pounds --.
Column 6, line 7, delete "chlamydials" and insert -- chlamydial--.
Column 7, line 37, delete "to" and insert -- is --; line 40, delete "a" and insert -- the --; line 42, delete "7"; line 57, delete "with" and insert -- on --.
Column 8, line 12 after "washes" insert -- should be used --; line 27, delete "american type culture collection" and insert -- American Type Culture Collection --; line 32, delete "than" and insert -- that --; line 56, after "hybridoma" insert -- having --.

Signed and Sealed this

Eighth Day of February, 1994

Attest:

BRUCE LEHMAN

*Attesting Officer*        Commissioner of Patents and Trademarks

UNITED STATES PATENT AND TRADEMARK OFFICE
CERTIFICATE OF CORRECTION

PATENT NO. : 5,212,062

DATED : May 18, 1993

INVENTOR(S) : Daniels et al.

It is certified that error appears in the above-identified patent and that said Letters Patent is hereby corrected as shown below:

On the cover page, in the Abstract, line 4, delete "than" and insert --that--.
Column 6, line 33, delete "sulface" and insert --sulfate--; line 62 delte "ethyleniamine" and insert --ethyleneamine--.

Signed and Sealed this

Fifth Day of April, 1994

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,212,062
DATED : May 18, 1993
INVENTOR(S) : Daniels et al.

It is certified that error appears in the above-indentified patent and that said Letters Patent is hereby corrected as shown below:

On the title page, under Assignee, after "University" insert — Research Foundation —.

Signed and Sealed this

Twenty-fifth Day of October, 1994

Attest:

BRUCE LEHMAN

*Attesting Officer*    *Commissioner of Patents and Trademarks*